United States Patent [19]

Pope, Jr. et al.

[11] Patent Number: 4,899,757
[45] Date of Patent: Feb. 13, 1990

[54] ULTRASOUND IMAGING PROBE WITH ZERO DEAD SPACE

[75] Inventors: Joseph L. Pope, Jr.; James M. Griffith; James M. Gessert, all of Newport Beach; Mario Maciel, Phelan; Paul Zalesky, Huntington Beach, all of Calif.

[73] Assignee: InterTherapy, Inc., Costa Mesa, Calif.

[21] Appl. No.: 158,761

[22] Filed: Feb. 22, 1988

[51] Int. Cl.[4] .................................................. A61B 8/12
[52] U.S. Cl. ........................... 128/662.06; 128/663.01
[58] Field of Search ....................... 128/662.06, 661.09, 128/663.01; 73/861.25, 623, 644

[56] References Cited

U.S. PATENT DOCUMENTS

| | | | |
|---|---|---|---|
| 4,541,433 | 9/1985 | Baudino | 128/662.06 X |
| 4,697,595 | 10/1987 | Breyer et al. | 128/662.06 |
| 4,732,156 | 3/1988 | Nakamura | 128/662.06 X |
| 4,757,821 | 7/1988 | Snyder | 128/662.06 X |
| 4,771,788 | 9/1988 | Millar | 128/662.06 X |

OTHER PUBLICATIONS

Yock, Paul G., "Catheter Apparatus", European Patent Application Publ. No. 0234951 publ. 02.09.87.
Martin; Roy W., "An Ultrasonic Catheter for Intravascular Measurement of Bloodflow: Technical Details", IEEE Trans. on Sonic & Ultrasonic, vol. 54-27, No. 6, Nov. 1980, pp. 277-286.
Hartley, C. J. et al., "A Pulsed Doppler Catheter for Measuring Coronary Artery Velocity", Proc. of the 26th Annula Conf. on Engry in Med. & Biol., Minneapolis, Minn. 9/30-10/4/73, p. 9.5.

Primary Examiner—Francis Jaworski
Attorney, Agent, or Firm—Nixon & Vanderhye

[57] ABSTRACT

An ultrasonic imaging probe includes a probe guide assembly, an ultrasonic transducer fixed to the distal end of the probe guide assembly, and electrical cabling housed within the probe guide assembly and operatively connected to the transducer for sending electrical pulse/signals to/from the transducer. The transducer is of a type which emits/receives ultrasonic waves along a path parallel to the elongate axis of the probe. The ultrasonic waves are directed radially of the probe by means of a reflector element which is distally spaced from the transducer along the probe's axis by a dimension sufficient to remove "dead space"(i.e., an area where ultrasonic imaging is not possible) radially of the catheter. An inductor coil (which tunes the transducer to the electrical cabling) is coaxially housed within the probe guide assembly closely adjacent the transducer and is electrically connected in series thereto. By removing the dead space radially of the catheter tube and by mounting an inductor coil closely adjacent the transducer within the probe guide assembly, a miniaturized ultrasonic imaging probe is provided which is especially useful for intravascular imaging/diagnostic procedures.

22 Claims, 2 Drawing Sheets ly-owned U.S. Patent Application Ser. No. 053,692 filed
ULTRASOUND IMAGING PROBE WITH ZERO DEAD SPACE

RELATED APPLICATION

This application is related to copending and commonly-owned U.S. Patent Application Ser. No. 053,692 filed May 26, 1987 in the name of Griffith et al, the entire content of which is expressly incorporated herein by reference.

FIELD OF THE INVENTION

This invention generally relates to ultrasonic intravascular imaging devices —i.e., devices of the type which utilize acoustic transducers operating at ultrasonic frequencies to image intravascular geometry and/or associated tissue characteristics. In a specific embodiment it includes an elongate probe guide assembly, an ultrasonic transducer fixed to the probe guide assembly's distal end, and electrical cabling housed within, and extending proximally of, the probe guide assembly so as to send/receive electrical signals to/from the transducer.

This invention effectively reduces "dead space" radially of the probe otherwise obscuring nearby reflections during the normal "ring down" time of a piezoelectric transceiver/transducer immediately after a transmit operation. A reflector is distally spaced from the transducer so as to reflect the ultrasound waves between a first path which is substantially parallel to the probe axis and a second path which is substantially perpendicular (i.e., radial) to the probe axis. A tuning induction coil is electrically connected in series with the transducer and is coaxially positioned within the tube section closely adjacent to the transducer. Such structure permits the ultrasound probes of this invention to be sufficiently miniaturized to be useful in extremely near-field intravascular imaging procedures.

BACKGROUND AND SUMMARY OF THE INVENTION

Intravascular probes which include ultrasound imaging crystal arrays have been proposed in the past. It is known, for example, to mount a piezoelectric crystal element (conventionally termed a "transducer") on or within a catheter of the type which can be inserted into a blood vessel. Once the probe has been inserted into a blood vessel, the transducer is electro-mechanically excited (as by the application of an electrical signal) to cause emission of ultrasonic energy into the surrounding tissue. While much of the emitted energy is absorbed by the surrounding tissue, a sufficient amount of energy is reflected back toward the transducer to permit imaging (with reflection occurring principally at interfaces between different types of material, e.g., the interface between blood and the vascular wall, the interface between blood and lesions adhered to the vascular wall, etcetera).

The transducer, in turn, produces weak electrical signals in response to electro mechanical excitation by the returning reflected ("echo") ultrasonic energy. These weak electrical signals can be used to determine the geometry and/or other characteristics of the blood vessel, for example, to determine whether or not the blood vessel contains lesions or other abnormalities. These determinations are usually termed "imaging" since suitable video and/or other signal monitoring equipment are employed to convert the weak electrical signals produced by the transducer into human-readable form. Information gained from such imaging thus may assist the physician in a vascular treatment in real time or in diagnosing a patient's particular ailment or disease so that suitable therapy can be prescribed.

One problem that has plagued conventional ultrasound imaging probes in the past is that an inherent "dead space" usually exists in the immediate vicinity of the transducer. That is, since considerable mechanical excitation (i.e., vibration) of the transducer occurs when ultrasonic energy waves are generated and emitted, it takes some time thereafter for the ringing crystal structure to quit vibrating sufficiently to permit detection of the much weaker echo reflections being returned to the transducer. Once this "dead" time is elapsed, the transducer can begin responding to received echo waves. The time it takes for the transducer to cease its strong electro mechanical transmit vibration (i.e., so that it can then begin sensible electro mechanical vibration in response to weaker echo waves) is sometimes termed the transducer "ring down" time. As can be appreciated, at any given transducer frequency of operation, more or less ring down time will inherently be present so that a region surrounding the transducer is effectively masked—that is to say, the ring down time creates a "dead space" in the immediate vicinity of the transducer where no imaging is possible.

The dimensional extent of such dead space is dependant upon many variables, including the frequency of operation of the transducer. Suffice it to say here that although transducer dead space can be tolerated when relatively large intravascular cavities are imaged (i.e., relative to the size of the imaging probe), significant problems are encountered when small intravascular cavities, such as small diameter blood vessels, etcetera, are to be imaged. And, in any event, transducer dead space mitigates against miniaturization since even the smallest diameter imaging probe is only capable of imaging intravascular cavities outside of its surrounding dead space, thereby providing for an effective imaging area which is usually only significantly greater than the probe's diameter.

Another problem which mitigates against imaging probe miniaturization is that the transducer must be "tuned" to the electrical cabling which supplies driving signals to, and returns weaker echo electrical signals from, the transducer. That is, since the transducer, at its frequency of operation, exhibits a net capacitive reactance, inductive reactance should be provided so as to efficiently couple the transmit/receive signals to the transducer (e.g., so as to maximize signal-to-noise ratios).

The present invention, however, provides a miniaturized ultrasonic imaging probe which not only exhibits essentially zero "dead space" (i.e., intravascular imaging can be accomplished in blood vessels having, or capable of being dilated to, substantially the same diameter as the probe itself) but also provides for internal (i.e., as part of the probe per se) inductive reactance. And, the fact that internal inductive reactance may now be provided enhances the ability to use weak electrical echo signals for purposes of diagnostic imaging.

These novel features of the invention are achieved by equally novel structure associated with an ultrasonic imaging probe of the type including a probe guide assembly, a transducer connected to the distal end of the probe guide assembly, and electrical cabling housed within the probe guide assembly and operatively connected to the transducer for transmitting electrical power to, and receiving electrical signals from, the transducer. The transducer is mounted within a proximal end portion of a generally cylindrical holder (itself being attached to the distal end of the probe guide assembly) which defines an elongate, open trough. Thus, the transducer is also mounted near the proximal end of the trough.

An ultrasound reflector (e.g., polished stainless steel) is mounted at the distal end of the holder (i.e., at the distal end of the defined trough) in axially spaced relation to the transducer for directing ultrasonic energy waves between a first path (which is substantially parallel to the elongate axis of the probe) to a second path (which is substantially perpendicular to the elongate axis of the probe). Thus, ultrasonic energy waves emitted from the transducer along the probe's elongate axis will be redirected radially of the probe by means of the reflector towards the surrounding tissue being imaged. Echo waves which radially return from the surrounding tissue will likewise be redirected by means of the reflector axially of the probe towards the transducer. The distance that the reflector is axially spaced from the transducer is selected such that the "dead space" lies substantially therebetween. Thus, since the dead space for any given transducer will lie axially between the transducer and the reflector, intravascular imaging immediately radially adjacent the external periphery of the probe is possible. That is, as long as the probe is of a size which is capable of being moved within intravascular tissue or organs, then imaging of such tissue or organs is possible.

The probe of the invention is also provided with an inductor coil as the inductive reactance, the inductor coil being coaxially housed within the probe guide assembly and positioned closely adjacent the transducer. Preferably, the electrical cabling of the invention is a standard coaxial cable having an inner conductor (with an associated insulating layer) and an annular outer conductor (with an associated insulating layer). According to this invention, a distal end segment of the outer conductor (and its associated insulating layer) is removed. The inductor coil is then coaxially positioned over the inner conductor (and its associated insulating layer) in the space previously occupied by the removed outer conductor segment. The proximal end of the inductor coil is thus connected to the distal end of the remaining outer conductor while the distal end of the inductor coil is connected electrically to the transducer. The inner conductor, on the other hand, is connected electrically to the transducer at a location different from the connection of the inductor coil (preferably at a location on the front face of the transducer). In such a manner, the transducer and inductor coil are connected closely adjacent, and in series relationship, to one another.

These as well as other objects and advantages of the invention will become apparent after careful consideration is given to the following detailed description of the presently preferred exemplary embodiments.

BRIEF DESCRIPTION OF THE ACCOMPANYING DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENT

Figure 1:
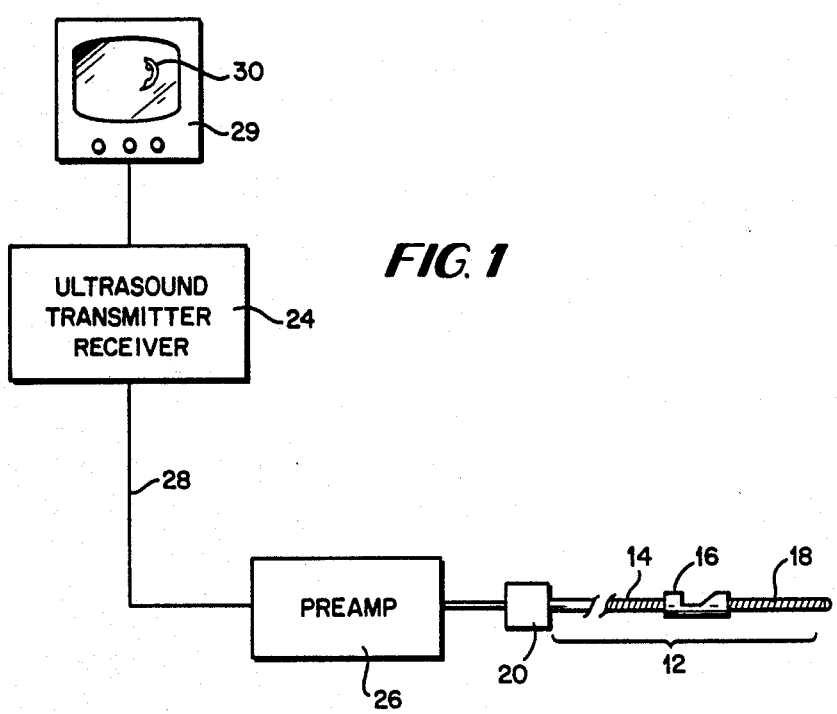
FIG. 1 is a schematic diagram of an exemplary ultrasound imaging system with which the ultrasound imaging probe of this invention is used.

A schematic diagram of an exemplary ultrasound imaging system 10 is shown in accompanying FIG. 1. System 10 generally includes an ultrasound imaging probe 12 (which will be described in greater detail below) generally comprised of proximal probe guide assembly 14, an ultrasound "bullet" 16 (i.e., structure which includes the ultrasound transducer), and a distal guidewire assembly 18. A visual position indicator and rotation knob 20 are operatively associated with the probe 12 so as to assist the physician in his/her intravascular manipulation and positioning of the bullet 16.

An ultrasound transmitter/receiver 24 is connected to a preamplifier 26 via standard coaxial cable 28. The transmitter/receiver 24 is of a conventional type in that it produces a pulse signal (of a desired magnitude and shape) which is applied via cable 28 and preamplifier 26 to excite an electroacoustic transducer housed within bullet 16. The receiver portion of transmitter/receiver 24 performs conventional signal processing operations (e.g., amplification, noise reduction and the like) on electrical signals generated by electro mechanical excitation of the transducer within bullet 16 (i.e., signals generated by the transducer in response to receiving echo waves), which signals have been amplified via preamplifier 26. These processed signals are then supplied as an input to a CRT 20 monitor (or any other equivalent display device) so as to generate an ultrasound image 30 representative of the vascular structures reflecting ultrasonic energy toward the transducer within bullet 16 using, for example, conventional PPI (radar) algorithms.

Figure 2:
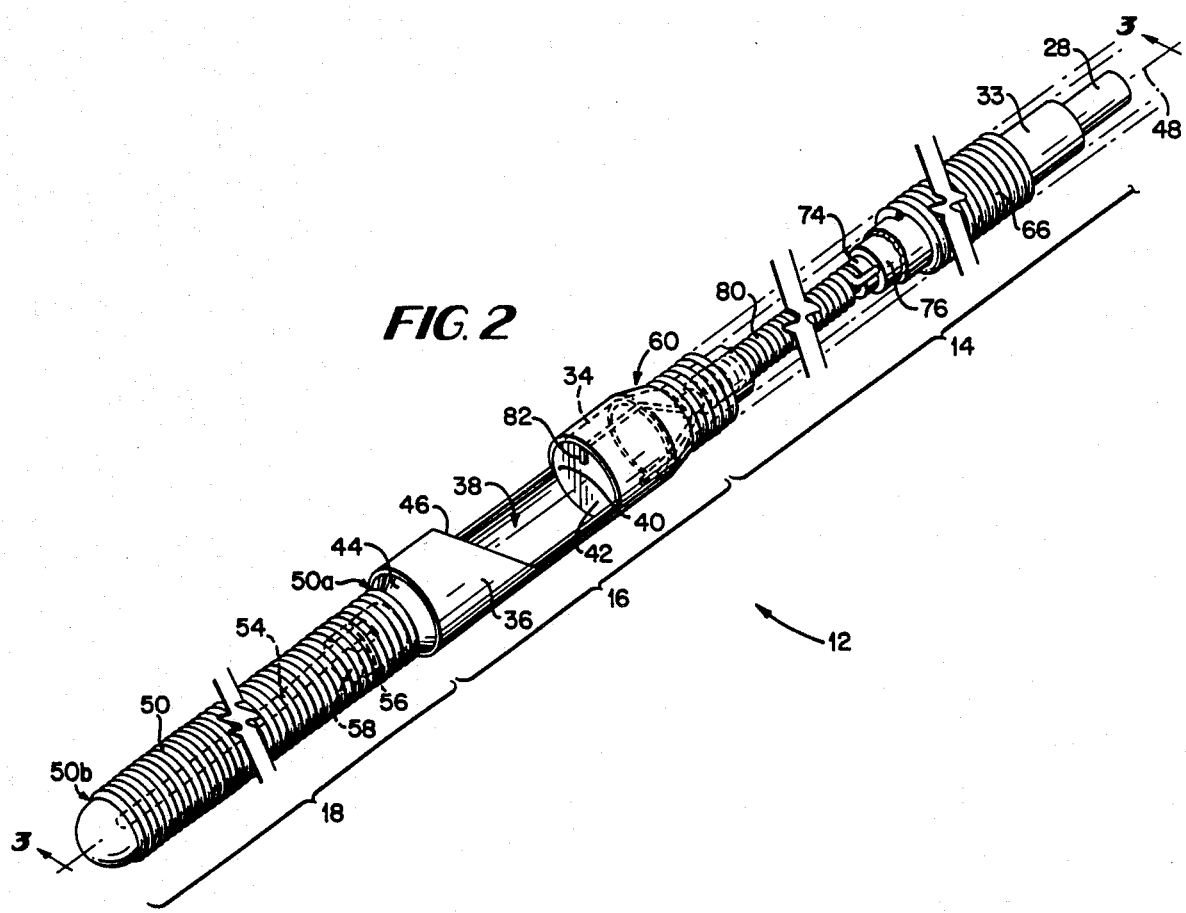
FIG. 2 is a perspective view, partly in section, of the ultrasound imaging probe of this invention.
Figure 3:
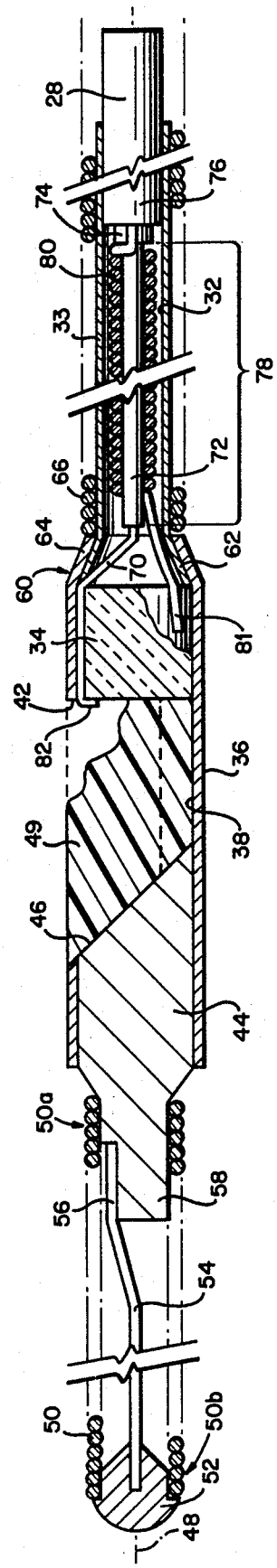
FIG. 3 is an axial cross-sectional view of the imaging probe shown in FIG. 2 taken along line 3—3 therein.

The imaging probe 12 of this invention is shown more clearly in accompanying FIGS. 2 and 3 in a greatly enlarged manner for clarity of presentation. For example, although the probe 12 can be of any desired length, it preferably is fabricated to a length of about 60 inches having a nominal diameter of about 0.0038 inch. As is seen, the probe guide assembly 14 is currently comprised of a coaxial cable 28 housed within the lumen 32 (see FIG. 3) of a tube section 33 so as to transmit electrical pulses to, and return electrical signals from, the transducer 34 housed within the bullet 16.

The bullet 16 is itself comprised of a one-piece holder 36 which defines an axially elongate open trough 38. The holder 36 thus houses the transducer 34 within its proximal end so that the front face 40 of transducer 34 extends slightly beyond the proximal end 42 of trough 38.

The other, distal end of holder 36 houses an acoustic reflector 44 (whose functions will be described in greater detail below) which in the preferred embodiment shown, defines a beveled planar surface 46 oriented at an angle (e.g., 45°) relative to the longitudinal axis 48 of probe 12. The surface 46 of reflector 44 may, however, be concave, particularly if convergent focussing of emitted/returned echo waves is desired. In either case, the angular orientation of surface 46 with respect to a transverse plane may be greater/lesser than 45° so as to project the reflected acoustic waves in a proximal/distal direction, respectively.

The acoustic reflector 44 and holder 36 are each preferably fabricated from stainless steel and are rigidly coupled to one another via soldering, welding or like techniques. The transducer 34, on the other hand, is rigidly maintained within holder 36 via a suitable biocompatible adhesive.

The positions of transducer 34 and reflector 44 within holder 36 could, however, be reversed from that shown in the accompanying FIGURES, if desired. Thus, transducer 34 could occupy the distal end of holder 36 while reflector 44 could occupy the proximal end of holder 36.

Preferably, the open trough 38 is filled with a solid acoustic couplant 49 which is shown only in FIG. 3 for clarity of presentation. Acoustic couplant 49 can be any suitable minimally acoustic-absorbant polymer material such as low density polyethlene, polyurethane, and the like. Couplant 49 thus exhibits an acoustic impedance which is closely matched to that of transducer 34 and the patient's blood. The acoustic couplant 49 also presents an overall smooth cylindrical exterior surface to holder 36 which is beneficial since the holder 36 may then be more easily manipulated within a patient's arterial tissue. Because it fills the trough 38, the acoustic couplant 49 prevents blood from pooling and clotting within holder 36, which clotting could cause patient thrombosis.

The distal guidewire assembly 18 is comprised of a coiled guidewire 50 (e.g., formed from about 0.003 in. diameter wire and tightly coiled to an outside diameter of about 0.038 in.) having its proximal end 50a rigidly coupled to the holder/reflector 36/44 as by soldering, welding or the like. A tip 52 of a noble metal (e.g., gold, platinum or the like) is formed by brazing, welding, or like techniques so as to embed the distal end 50b of guidewire 50. Tip 52 presents a smooth convex surface to more easily facilitate intravascular maneuvering. Also, since the tip 52 is formed of a noble metal, it is visible when fluoroscopic techniques are employed.

The tip 52 also embeds the distal end of a continuous safety ribbon 54. The proximate end of ribbon 54 is soldered or welded rigidly to an axially bevelled surface 56 of a generally cylindrical, distally extending boss 58 integral with reflector 44. The ribbon 54 thus provides an added measure of safety to ensure that the assembly 18 will not inadvertently become separated from the catheter 12 during use.

The proximal end of holder 36 is rigidly connected to the distal end of tube section 33 via a "trumpet-shaped" connecting region 60. That is, the tube section 33 includes an outwardly (i.e., in the distal direction) flared region 62 coupled to the interior of an inwardly (i.e., in a proximal direction) tapered region 64 of the holder 36. The region 64 thus surrounds and is rigidly coupled (as by soldering, welding, or the like) to the region 62 so as to prevent separation of the holder 36 and tube section 33 during intravascular manipulations. Preferably, the tube section 33 is formed of stainless steel and dimensioned so as to be about six(6) inches in length and have about a 0.028 in. outside diameter and about a 0.023 in. inside diameter. Thus, the tube section 33 is thin-walled (e.g., about 0.0025 in. thick) such that it is flexible (bendable) relative to the catheter axis 48.

The tube section 33 is surrounded by another coiled guide wire 66 and extends proximally beyond the axial length of tube section, 33 (i.e., to the exterior of the patient). Guide wire 66 functions to support tube 33 (i.e., so as to provide increased strength) so as to prevent kinks from forming in the otherwise thin-walled tube 33 when it is manipulated during intravascular imaging. By way of example, the guide wire 66 is formed of a tightly coiled wire approximately 0.005 in. in diameter so that the resulting inside diameter of the coil is about 0.0028 inch.

As is best seen in FIG. 3, the coaxial cable 28 is of a conventional type in that it includes a center conductor 70 (and its associated insulating layer 72) and an annular (i.e., braided shield) outer conductor 74 (and its associated outer insulating layer 76). The inner and outer conductors are preferably copper, but other electrically conductive materials may be employed provided that the impedance of the cable is sufficient for purposes of ultrasound imaging. In this regard, the coaxial cable 28, in the preferred embodiment, will exhibit an impedance of about 25 or 50 ohms.

A distal segment 78 (see FIG. 3) of the outer conductor/insulating layer 74/76 is removed according to this invention and, in its place, an inductor coil 80 is positioned coaxially surrounding the underlying inner conductor/insulating layer 70/72. The proximal end of inductor coil 80 is electrically connected to the terminal end of the outer conductor 76 while the other distal end of inductor coil 80 is electrically connected via a soldered flat copper ribbon 81 (about 0.01 in. wide by 0.001 in. thick) to the peripheral exterior surface of transducer 34 (or at any other suitable location). The terminal end of the center conductor 70, on the other hand, is electrically coupled via a soldered flat copper ribbon 82 (similar to ribbon 81), to the front face 40 of transducer 34 (i.e., at a location different from that of the electrical connection of ribbon 81, and hence coil 80). The inductor coil 80 is therefore series-connected to the transducer 34.

The particular characteristics of coil 80 are chosen so as to "tune" the signal carrying capability of cable 28 to the operating characteristics of the transducer 34. That is, the wire diameter, coil size, number of turns, etcetera, are selected so that the overall performance of the inductor coil 80 is such that it exhibits an inductive reactance which is substantially equivalent to the net capacitive reactance of the transducer 34 at its operating frequency. In the preferred embodiment, coil 80 will be formed of about 0.005 in. diameter single strand, ML (DuPont TM ) coated copper wire and coiled to an outside diameter of about 0.020 in. and a length of about 2.8 inches. Such an inductor coil will exhibit an inductive reactance of about 100 ohms at 20 MHz (i.e., an inductance of about one microHenry). Since the inductor coil 80 is located closely adjacent the transducer 34, an effectively increased signal to noise ratio results with the benefit being that higher quality imaging signals are transmitted into the receiver portion of the transmitter/receiver 24.

In use, the probe 12 is intravascularly inserted into a patient. For example, if the catheter 12 is to be used so as to image a patient's coronary arteries, then it may conveniently be inserted percutaneously into the patient's femoral artery. The catheter 12 is then maneuvered by the physician until a desired region of the patient's coronary arteries is adjacent the bullet 16, such maneuvering being aided by the position indicator and rotation knob 20 (see FIG. 1) in addition to the fluoroscopically visible tip 52 (i.e., if fluoroscopic imaging techniques are also employed).

With the bullet 16 properly positioned, ultrasound imaging of the adjacent arterial tissue may be accomplished conventionally by sending electrical pulses to and receiving electrical signals from, transducer 34 as has been previously described. The transmission of ultrasound waves to/from transducer 34 may be aided by the presence of blood and/or other body fluids in trough 38, which fluids serve to acoustically couple the transducer 34 and reflector 44. Also, the "dead space" (i.e., that region in advance of the transducer 34 in which no imaging is possible) will be located substantially in that area between the transducer 34 and the reflector 44 and hence ultrasound imaging of the surrounding arterial tissue within a minimum imaging region established by the exterior periphery of the holder 36 is possible.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An ultrasonic imaging probe comprising:
an elongate probe guide assembly;
transducer means connected near a distal end of said probe guide assembly for transmitting/receiving ultrasonic waves along a first path; and
electrical cable means which includes a two lead cable housed within said probe guide assembly and operatively connected to said transducer means for transmitting electrical signals to, and receiving electrical signals from, said transducer means;
said electrical cable means including an inductor coil coaxially housed within said probe guide assembly and having proximal and distal ends, said inductor coil being positioned closely adjacent said transducer means such that said inductor coil distal end is electrically connected to said transducer means, and wherein
one of said leads of said cable being electrically connected to said proximal end of said inductor coil, and another of said leads of said cable being electrically connected to said transducer means at a location different from said electrical connection of said inductor coil distal end thereto, whereby said one cable lead, inductor coil, transducer means and said other cable lead are in series connection.

2. An ultrasonic imaging probe as in claim 1, further comprising:
a holder for said transducer means which defines an elongate trough which establishes an axis, said transducer means being housed by said holder at one end of said trough for transmitting/receiving ultrasonic waves along said established axis; and
reflector means rigidly coupled to said holder at the other end of said trough for reflecting incident ultrasonic waves between a first path which is substantially parallel to said established axis, and a second path which is angularly oriented with respect to the axis of said probe, whereby said ultrasonic waves transmitted by said transducer means along said first path are reflected by said reflector means along said second path towards an object to be imaged, and echo ultrasonic waves returning along said second path from said object to be imaged are reflected by said reflector means along said first path.

3. An ultrasonic imaging probe as in claim 2, wherein said reflector means includes a polished planar surface oriented at an angle of substantially 45° with respect to the axis of said probe, said incident ultrasonic waves being reflected by means of said polished planar surface between said first and second paths, such that said second path is radially oriented with respect to said established axis.

4. An ultrasonic imaging probe comprising an elongate probe guide section, and an ultrasonic transmitting/receiving section coaxially connected to a distal end of said probe guide section, wherein
(a) said ultrasonic transmitting/receiving section includes;
a generally cylindrical holder defining an open trough;
reflector means rigidly coupled to said holder at a distal end of said trough for reflecting incident ultrasonic waves between a first path which is substantially parallel to the axis of said probe, and a second path which is substantially perpendicular to the axis of said probe;
ultrasound transducer means rigidly coupled to said holder at a proximal end of said trough for propagating ultrasonic waves towards, and receiving ultrasonic waves from, said reflector means along said first axial path; and wherein
(b) said probe guide section includes;
a tube portion having its distal end coaxially connected to a proximal end of said holder;
an inductor coil coaxially positioned within said tube portion and having its distal end electrically connected to said transducer means; and
at least a two lead electrical cable means at least partially housed within said tube portion for transmitting electrical signals to and receiving electrical signals from said transducer means,
one of said leads being connected to said transducer means and the other of said leads being electrically connected to a proximal end of said inductor coil.

5. An ultrasonic imaging probe comprising:
a probe guide having proximal and distal probe guide assemblies, and a holder coaxially positioned between said proximal and distal probe guide assemblies;
an ultrasonic transducer mounted within said holder;
means for connecting said holder to axially distal and proximal ends of said proximal and distal probe guide assemblies, respectively; and
electrical cable means positioned within said proximal probe guide assembly and operatively coupled to said transducer for transmitting electrical signals to/from said transducer, wherein
said proximal probe guide assembly includes an elongate tube section having a distal end connected to a proximal end of said holder and extending proximally from said holder, said cable means being positioned within said tube section;
said means for connecting includes;
(i) a region formed at said distal end of said tube section which is outwardly flared in a distal direction; and
(ii) a region formed at a proximal end of said holder which is inwardly flared in a proximal direction, said inwardly flared region surrounding said outwardly flared region of said tube section, and being rigidly affixed thereto, and wherein;

said distal probe guide assembly includes;
(i) a distally projecting boss formed on said holder distal end, said boss having an axially bevelled surface;
(ii) a tip having a smooth convex distal surface;
(iii) a coiled distal guidewire having a distal end rigidly affixed to said tip, and a proximal end rigidly fixed to and surrounding said distally projecting boss of said holder distal end; and
(iv) a safety ribbon positioned within said coiled guidewire and having a distal end which is rigidly affixed to said tip and a proximal end which is rigidly affixed to said axially bevelled surface of said distally projecting boss.

6. An ultrasonic imaging probe as in claim 5, further comprising
an inductor coil coaxially housed within said tube section and having its distal end electrically connected to said transducer, and wherein,
said cable means includes at least two leads, one said lead being connected to said transducer and the other of said leads being connected to a proximal end of said inductor coil.

7. An ultrasonic imaging probe as in claim 5 or 6, wherein said holder is generally cylindrical and defines an open elongate trough region, said transducer being rigidly housed within said holder at a proximal end of said trough region.

8. An ultrasonic imaging probe as in claim 7, further comprising reflector means rigidly housed within said holder at a distal end of said trough region and coaxially positioned with respect to said transducer for reflecting ultrasonic waves transmitted by said ultrasonic transducer at substantially right angles to the elongate axis of said probe.

9. An ultrasonic imaging probe as in claim 8, wherein said reflector means includes a polished planar surface oriented at an angle of substantially 45° relative to the elongate axis of said probe.

10. An ultrasonic imaging probe as in claim 5, further comprising second guide wire means having a distal end connected to a proximal end of said holder and proximally extending therefrom in surrounding relationship to said tube section.

11. An ultrasonic imaging probe comprising:
a probe guide;
a holder;
an ultrasonic transducer mounted within said holder;
means for connecting said holder to an axially distal end of said probe guide; and
electrical cable means positioned within said probe guide for transmitting electrical signals to/from said transducer, wherein
said means for connecting includes;
(i) a tube section;
(ii) an outwardly flared region formed at a distal end of said tube section; and
(iii) an inwardly tapered region formed at a proximal end of said holder and surrounding said outwardly flared region of said tube section;
said imaging probe further comprising guide wire means including an axially flexible coiled guide wire connected to and coaxially extending in advance of said holder for assisting in the guiding and manipulation of said probe during use, said guide wire means including a tip at the distal end thereof, and a continuous safety ribbon positioned within said coiled guide wire and having one end rigidly fixed to said tip and another end rigidly attached to a distal end of said holder, and wherein
said holder at said distal end thereof includes a distally projecting cylindrical boss having an axially bevelled surface, said another end of said safety ribbon being rigidly attached to said bevelled surface of said boss.

12. An ultrasonic imaging probe comprising:
a probe guide;
a holder;
an ultrasonic transducer mounted within said holder;
means for connecting said holder to an axially distal end of said probe guide; and
electrical cable means positioned within said probe guide for transmitting electrical signals to/from said transducer, wherein
said means for connecting includes;
(i) a tube section;
(ii) an outwardly flared region formed at a distal end of said tube section; and
(iii) an inwardly tapered region formed at a proximal end of said holder and surrounding said outwardly flared region of said tube section;
said imaging probe further comprising;
an inductor coil coaxially housed within said tube section and having its distal end electrically connected to said transducer, and wherein,
said cable means includes at least two leads, one said lead being connected to said transducer and the other of said leads being connected to a proximal end of said inductor coil, and wherein
said cable means is a coaxial cable having (a) an inner electrically conductive lead, forming said one lead of said cable means, which is surrounded by an inner electrically insulative layer, and (b) an outer electrically conductive lead, forming said another lead of said cable means, which is surrounded by an outer electrically insulative layer, and wherein said outer electrically conductive lead and insulative layer annularly surround said inner electrically conductive lead and insulative layer, and wherein said inner lead is connected to said transducer and said outer lead is connected to said proximal end of said inductor coil.

13. An ultrasonic imaging probe as in claim 12, further comprising means associated with said coaxial cable for establishing an axial mounting space for said inductor coil so that said inductor coil and coaxial cable are each positioned within said tube section, said mounting space establishing means being provided by an axially removed region of said outer electrically conductive lead and insulative layer to thereby expose a corresponding axial region of said inner electrically conductive lead and insulative layer, wherein said inductor coil occupies the space of said removed region of said outer electrically conductive lead and insulative layer such that said inductor coil annularly surrounds said exposed corresponding axial region of said inner electrically conductive lead and insulative layer.

14. An intravascular ultrasonic imaging probe comprising:
an elongate probe guide assembly establishing a probe axis;
a holder defining an open trough;
said probe guide assembly and said holder being of a sufficiently miniaturized diameter so as to allow said probe guide assembly and holder to be inserted into a vessel of a patient's vascular system having, or capable of being dilated to, substantially the same diameter as the diameter of said probe guide assembly and said holder;

an ultrasound reflector rigidly coupled to said holder at a distal end of said trough for reflecting incident ultrasonic waves between a first path which is parallel to said probe axis and a second path which is radial to said probe axis; and an ultrasound transducer rigidly coupled to said holder at a proximal end of said trough which mechanically vibrates during a transmit cycle for propagating ultrasonic waves towards said reflector along said first path, and which mechanically vibrates during a receive cycle in response to receiving ultrasonic waves from, said reflector along said first path, and wherein said reflector is axially distally spaced from said transducer by a fixed predetermined dimension to allow, for a given frequency of operation of said transducer, said mechanical vibration of said transducer during said transmit cycle to essentially cease prior to said mechanical vibration occurring during a receive cycle such that an area where ultrasonic imaging is not possible for said given frequency lies between said transducer and reflector and thus permits said probe to perform ultrasonic imaging immediately radially adjacent an external periphery of said holder.

15. An ultrasonic imaging probe comprising:
an elongate probe guide assembly establishing a probe axis;
a holder assembly defining an open trough;
an ultrasound reflector rigidly coupled to said holder at one end of said trough for reflecting incident ultrasonic waves between a first path which is substantially parallel to said probe axis and a second path which is angularly oriented with respect to said probe axis;
an ultrasonic transducer rigidly coupled to said holder at another end of said trough so that said transducer is in axially spaced relation to said reflector, said transducer for propagating ultrasonic waves towards, and receiving ultrasonic waves from, said reflector along said first path; and
a solid ultrasonic couplant medium filling said trough in the space between said transducer and reflector.

16. An ultrasonic imaging probe as in claim 15, wherein said solid ultrasonic couplant medium consists essentially of a polymeric material which is substantially non-absorbant to said ultrasonic waves.

17. An ultrasonic imaging probe as in claim 15, wherein said holder is generally cylindrical in configuration, and wherein said holder and said solid couplant medium collectively define a continuous smooth cylindrical outer surface.

18. An ultrasonic imaging probe comprising:
ultrasonic transducer means for propagating and receiving ultrasonic waves along a predetermined axis;
ultrasonic reflector means spaced from said transducer means along said predetermined axis for redirecting incident ultrasonic waves between a first path coincident with said predetermined axis, and a second path which is angularly oriented with respect to said predetermined axis, whereby said ultrasonic waves propagating from said transducer means along said first path are redirected along said second path towards an object to be imaged, and ultrasonic waves returning from an object to be imaged along said second path are redirected along said first path towards said transducer means; and
solid couplant means positioned between said transducer means and said reflector means in said predetermined axis for acoustically coupling said transducer and reflector means with minimal attenuation of said ultrasonic waves.

19. An ultrasonic imaging probe comprising:
an elongate probe guide assembly;
transducer means connected near a distal end of said probe guide assembly for transmitting/receiving ultrasonic waves; and
electrical cable means housed within said probe guide assembly and operatively connected to said transducer means for transmitting electrical signals to, and receiving electrical signals from, said transducer means;
said electrical cable means including an inductor coil coaxially housed within said probe guide assembly, said inductor coil being positioned closely adjacent said transducer means and having a distal end connected therewith;
said cable means being a coaxial cable having (a) an inner electrically conductive lead surrounded by an inner electrically insulative layer, and (b) an outer electrically conductive lead surrounded by an outer electrically insulative layer, said outer electrically conductive lead and insulative layer annularly surrounding said inner electrically conductive lead and insulative layer, and wherein
said inner lead is connected to said transducer means and said outer lead is connected to a proximal end of said inductor coil.

20. An ultrasonic imaging probe comprising:
an elongate probe guide assembly;
a transducer means connected near a distal end of said probe guide assembly for transmitting/receiving ultrasonic waves; and
electrical cable means housed within said probe guide assembly and operatively connected to said transducer means for transmitting electrical signal to, and receiving electrical signals from, said transducer means, said electrical cable means including;
(i) a coaxial cable having (a) an inner electrically conductive lead connected to said transducer and surrounded by an inner electrically insulative layer, and (b) an outer electrically conductive lead surrounded by an outer electrically insulative layer, said outer electrically conductive lead and insulative layer annularly surrounding said inner electrically conductive lead and insulative layer;
(ii) an inductor coil having a proximal end connected to said outer lead, and a distal end connected to said transducer at a location different from the connection of said inner lead to said transducer; and
(iii) means associated with said coaxial cable for establishing a mounting space for said inductor coil so that said inductor coil and coaxial cable are each coaxially positioned within said probe guide assembly, said mounting space establishing means being provided by an axially removed region of said outer lead and outer insulative layer to thereby expose a corresponding axial region of said inner insulative layer, wherein said inductor coil occupies the space of said removed region of said outer lead and outer insulative layer such that said inductor coil annularly surrounds said exposed corresponding axial region of said inner insulative layer.

21. An ultrasonic imaging probe comprising:

an elongate probe guide assembly having a probe axis;

transducer means connected near a distal end of said probe guide assembly for transmitting/receiving ultrasonic waves, said transducer means including (a) an ultrasonic transducer for transmitting/receiving said ultrasonic waves along a first path which is substantially parallel to the probe axis, and (b) reflector means axially spaced from said transducer for reflecting incident ultrasonic waves between said first path and a second path which is substantially perpendicular to the probe axis, said reflector means at a distal end thereof including a distally projecting cylindrical boss having an axially bevelled surface;

electrical cable means housed within said probe guide assembly and operatively connected to said transducer means for transmitting electrical signals to, and receiving electrical signals from, said transducer means; and guide wire means extending in advance of said transducer means for assisting in the guiding and manipulation of said probe during use, said guide wire means including a safety ribbon having a proximal end which is rigidly attached to said bevelled surface of said boss.

22. An ultrasonic imaging probe comprising:

an elongate probe guide assembly;

a holder attached to a distal end of said probe guide assembly;

ultrasonic transducer means housed within said holder for transmitting/receiving ultrasonic waves; and distal guide assembly attached to, and distally extending in advance of said holder for assisting in the guiding and manipulation of said probe during use, said guide assembly including (a) a coiled guidewire having proximal and distal ends, said proximal end being rigidly affixed to said holder distal end, and (b) a tip presenting a smooth convex distal surface and rigidly affixed to said guidewire distal end; wherein said guide assembly further includes a safety ribbon having proximal and distal ends rigidly affixed to said holder and said tip, respectively, said safety ribbon being positioned within said coiled guidewire, and wherein said holder includes a distally extending boss having an axially bevelled surface, and wherein said proximal end of said coiled guidewire surrounds said boss, and said proximal end of said safety ribbon is rigidly affixed to said bevelled surface.

* * * * *